United States Patent [19]

Shank

[11] Patent Number: 5,195,535
[45] Date of Patent: Mar. 23, 1993

[54] DETACHABLE GUIDEWIRE EXTENSION

[75] Inventor: Peter J. Shank, Burlington, Mass.

[73] Assignee: C. R. Bard, Inc., Murray Hill, N.J.

[21] Appl. No.: 850,149

[22] Filed: Mar. 12, 1992

Related U.S. Application Data

[63] Continuation of Ser. No. 612,108, Nov. 9, 1990, abandoned.

[51] Int. Cl.$^5$ .............................................. A61B 5/00
[52] U.S. Cl. ..................................... 128/772; 128/657
[58] Field of Search ................ 128/657, 772; 604/95, 604/164, 283, 905

[56] References Cited

U.S. PATENT DOCUMENTS

| | | | |
|---|---|---|---|
| 1,994,303 | 3/1935 | Clark | 208/115 |
| 2,874,981 | 2/1959 | Brady | 604/283 |
| 3,787,126 | 1/1974 | Arlen | 403/104 |
| 4,790,825 | 12/1988 | Bernstein et al. | 128/657 |
| 4,820,288 | 4/1989 | Isono | 604/905 |
| 4,827,941 | 5/1989 | Taylor et al. | 128/657 |
| 4,846,193 | 7/1989 | Tremulis et al. | 128/772 |
| 4,875,489 | 10/1989 | Messner et al. | 128/657 |
| 4,917,103 | 4/1990 | Gambale et al. | 128/772 |
| 4,922,923 | 5/1990 | Gambale et al. | 128/657 |
| 4,955,858 | 9/1990 | Drews | 128/657 |

FOREIGN PATENT DOCUMENTS

| | | | |
|---|---|---|---|
| 0347035 | 6/1988 | European Pat. Off. | |
| 0674943 | 8/1990 | Switzerland | 128/772 |

Primary Examiner—Max Hindenburg
Attorney, Agent, or Firm—Wolf, Greenfield & Sacks

[57] ABSTRACT

A connection system for a guidewire and a guidewire extension includes a manually actuable locking mechanism for locking or unlocking the mated ends of the wires together. One of the mating ends includes a socket. The other mating end includes a wire having a reduced diameter end portion that carries a sleeve. An enlarged wedging element is attached to the tip of the wire. The arrangement of the wedging element and sleeve are insertable into the socket and, after insertion, the arrangement is manipulated to draw the wedging element into the end of the sleeve. The sleeve thus is wedged radially outwardly into firm engagement with the inner surface of the socket. The lock is easily released by pulling the sleeve axially away from the wedging element.

22 Claims, 4 Drawing Sheets

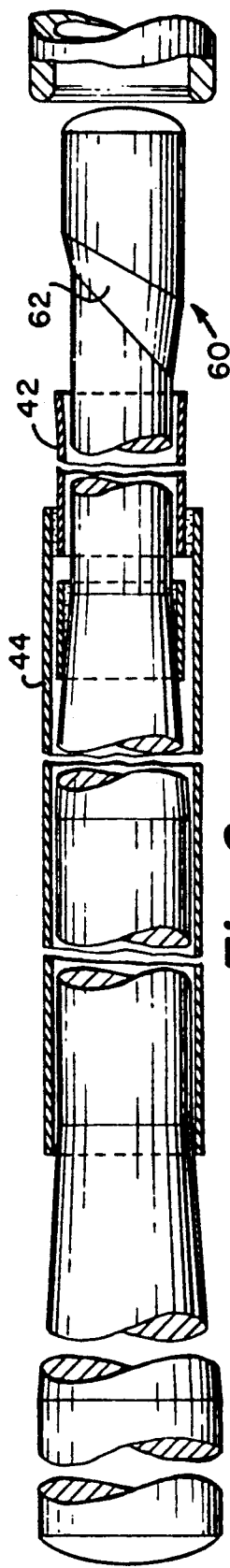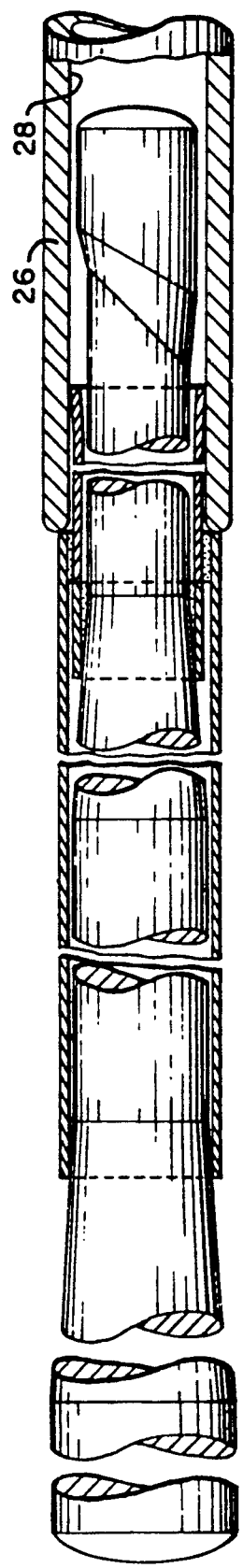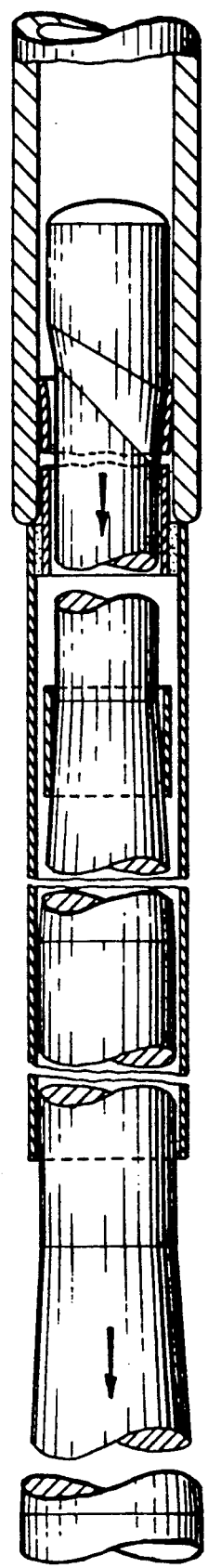

DETACHABLE GUIDEWIRE EXTENSION

This application is a continuation, of application Ser. No. 07/612,108, filed Nov. 9, 1990, now abandoned.

FIELD OF THE INVENTION

This invention relates to guidewires used in guiding of catheters and to devices and techniques for extending the effective length of the guidewires to facilitate catheter exchanges.

BACKGROUND OF THE INVENTION

In some catheterization techniques, it is desirable to use a series of catheters in order to complete effectively the procedure at hand. For example, in percutaneous transluminal coronary angioplasty procedures, in which a balloon catheter is advanced into an obstructed (stenosed) region of the patient's coronary artery and is inflated within the stenosis to dilate the lumen of the artery, it is not uncommon for the physician to require the sequential use of several balloon dilatation catheters having balloons of progressively increasing size. Typically, such catheters are used in connection with a guidewire that extends through the catheter and serves as a guide over which the catheter may be advanced to the stenosis. When performing such a catheter exchange, it is important to do so without shifting and losing the position of the guidewire so that the guidewire may be used to guide the next catheter to the stenosis.

In order to maintain guidewire position during a catheter exchange, conventional practice has been to use a relatively long exchange wire. The exchange wire, which typically is of the order of 300 cm long (as compared to a conventional guidewire length of the order of 180 cm), is first exchanged for the conventional indwelling guidewire by removing the indwelling guidewire from the existing catheter and replacing it with the longer exchange wire. Then the existing catheter is withdrawn over the exchange wire, the exchange wire being sufficiently long so that it is never completely covered by the withdrawn catheter, thereby enabling the exchange wire to be held in position by the physician or an assistant during the catheter withdrawal. After the initial catheter is removed, the succeeding catheter is advanced over the exchange wire which guides the second catheter to the stenosis. The exchange wire then may be removed and may be replaced with a conventional guidewire which, typically, will be more easily manipulated during the angioplasty procedure.

The foregoing procedures are time consuming and somewhat awkward. A significant advance in the technique for effecting catheter exchanges has been developed and involves a system that enables exchange of catheters without using exchange wires. In brief, that system utilizes an extension wire that is attached to the proximal end of the guidewire already in place in the patient. That effectively extends the overall length of the guidewire to that needed for the catheter exchange. The system is described in U.S. Pat. No. 4,917,103 issued Apr. 17, 1990 (Gambale). It uses a connection in which the distal end of an extension wire is telescoped together with the proximal end of the guidewire and the junction then is crimped, thus, retaining the wires together. With the crimped connection, when the guidewire and extension wire are detached, their reconnection is impaired because of the deformation formed during their connection. Thus, some inconvenience is presented should it be desirable to make multiple catheter exchanges.

Several devices have been designed for enabling reconnectible detachment of the guidewire and extension. Such devices are disclosed in U.S. Pat. No. 4,827,941 (Taylor) and in European Patent Application 89304257.2 published Dec. 20, 1989 (Palermo). The Taylor device discloses a connector for a guidewire and guidewire extension in which one of the members is provided with a tubular socket at one mating end and the other member is provided, at its mating end, with a serpentine like, undulating male member insertable into the socket. The diameter defined by the socket is less than the diameter defined by the male element so that the male element can be forced into the tubular element and be retained in the tube by friction. Among the difficulties with this arrangement is that the connector elements may not be retained together with the degree of security that may be desired. The extent to which the frictional forces retain the male element and socket together is limited by the maximum permitted connection force. The connection forces necessarily are limited because the parts are very small and delicate and could become damaged if too great a force were applied to them. It is not uncommon for the guidewire and guidewire extension, so connected, to become separated, either from manipulation of the guidewire or by being dragged apart by a catheter during removal of the catheter is a catheter exchange.

The invention described in the above mentioned European patent application (Palermo) provides a still further improvement in that the connection between the guidewire and extension includes a male member insertable easily and under low force into a receptive socket. The connection, however, is not a frictional connection but rather results in a mechanical interlock that will not separate when subjected to axial tension. More specifically, the connection system utilizes a telescoping connector that is self latching, disconnectible and reconnectible without deformation of the guidewire or the extension. In this arrangement the guidewire is provided with a tubular socket on the proximal end. The extension wire includes a shaft having a distal end that is surrounded by a helical coil, formed from rectangular cross section wire. The coil is attached to the extension wire shaft at the distal end of the coil and is free at the proximal end of the coil to enable the coil to stretch and contract about the shaft. The distal end of the extension wire carrying the coil is easily insertable under low force into the socket on the proximal end of the guidewire but self-locks in the socket and cannot be easily withdrawn. Application of axial tension to the guidewire and extension wire causes the edges of the rectangular cross-section wire to mechanically dig into the inner surface of the socket, thus precluding separation of the guidewire and extension wire. The extension wire and guidewire may be disconnected easily, however, by twisting the guidewire extension while simultaneously withdrawing it axially from the socket. The twisting motion frees the locking engagement of the helical coil with the internal surface of the socket.

Although the Palermo device represents a significant improvement it nevertheless presents some limitations. The structural configuration of the coil is such as to impose practical lower limits on the size of guidewire and extension with which that connection can be used.

In particular, it has been found to be difficult to use the coil-type of connection with guidewires smaller than 0.014" in diameter. Another difficulty that sometimes has been encountered is that when the physician's hands (wearing surgical gloves) become wet, as is common during an angioplasty procedure, it may be difficult to get a sufficient grip on the small diameter guidewire extension to twist it in order to free the locking engagement of the coil.

It would be desirable, therefore, to provide a guidewire and extension system having the attributes and advantages of the Palermo system but in an arrangement capable of use with smaller diameter guidewires. It also would be desirable to provide such a guidewire extension system in which the unlocking of the guidewire extension to the guidewire can be effected more easily. It is among the objects of the invention to provide such an improved device.

SUMMARY OF THE INVENTION

In accordance with the present invention, a connection system for a guidewire and guidewire extension utilizes an arrangement in which a sleeve, carried by one of the guidewire or extension is insertable into the tubular socket on the other of the guidewire or extension and is caused to expand radially outwardly into secure locking engagement with the inner surface of the tubular socket. In particular, the mating, distal end of the guidewire extension wire (or the proximal end of the guidewire, if the connector elements are reversed) is provided with a reduced diameter distal portion on which a thin walled polymeric sleeve is slidably mounted. The distal end of the the extension, including the distal portion of the polymeric sleeve is insertable into the tubular socket on the proximal end of the guidewire, with the proximal end of the sleeve, being exposed and accessible to the physician. The distal tip of the reduced diameter distal portion of the extension includes a slightly enlarged wedging element dimensioned so that it may be drawn toward and wedged inside of the distal end of the polymeric sleeve to cause the polymeric sleeve to expand radially outwardly. The wedging action is effected by causing relative axial motion of the extension with respect to the sleeve, such as by holding the sleeve in place (by its exposed end) while withdrawing proximally the extension wire to draw the wedging element into the distal open end of the sleeve. The tubing from which the socket at the proximal end of the guidewire is formed preferably is of the seamed tubing type in which the inner surface is relatively rough, thereby enhancing the grip between the sleeve and the inner surface of the tubular socket.

The connection resulting from the foregoing arrangement is strong and will withstand separation forces in excess of those normally encountered in actual use, thereby assuring that the guidewire and extension wire will not become inadvertently separated. The connection may be released easily by grasping the exposed proximal end of the sleeve and pulling the sleeve proximally to withdraw the distal end of the sleeve out from between its wedged engagement between the wedging element and the inner surface of the tubular socket. Alternately, the connection may be released by grasping the exposed proximal end of the sleeve and urging the extension wire in a distal direction.

All of the elements at the distal end of the guidewire extension, including the sleeve, and the wedging element are of a relaxed (unlatched) diameter that is approximately equal to or smaller than the diameter of the socket on the guidewire. Thus, there is no substantial resistance to mating of the guidewire and guidewire extension and the force required to mate them is very low. The strength of the connection, however, once locked, is very substantial. Additionally, because the sleeve may be formed with a very thin wall, it is possible to incorporate the present latching arrangement in very small diameter guidewires, possibly as low as 0.010" diameter. Additionally, the axial motion required to actuate the sleeve (either to lock or unlock the device) is easily effected.

It is among the general objects of the invention to provide an improved guidewire extension system.

A further object of the invention is to provide an improved guidewire extension system in which the guidewire and extension are disconnectible and reconnectible.

Another object of the invention is to provide a connection system for a guidewire and guidewire extension which incorporates improved means for locking the guidewire to the guidewire extension.

Another object of the invention is to provide a connection system for a guidewire and guidewire extension in which the locking system may be implemented by axial movement of a locking element.

A further object of the invention is to provide a connection system for a guidewire and guidewire extension of the type described in which the force required for mating connection is insignificant as compared to the strength of the resulting connection.

Another object of the invention is to provide a connection system for a guidewire and an extension wire of the type described in which the strength of the connection between the two increases in response to tension applied to the connection.

A further object of the invention is to provide a connection system for a guidewire and extension wire of the type described in which one of the wires carries an element capable of radial expansion and in which the system includes a means for effecting the radial expansion while the element is confined within a tubular socket on the other of the wires.

Still another object of the invention is to provide a connection system for a guidewire and guidewire extension of the type described which is suited for use with very small diameter guidewires, while also reducing the risk of kinking of the connector elements.

DESCRIPTION OF THE DRAWINGS

The foregoing and other objects and advantages of the invention will be appreciated more fully from the following further description thereof, with reference to the accompanying drawings wherein:

FIG. 9 is a fragmented, sectional illustration of another embodiment of the extension wire in accordance with the invention;

FIG. 10 is a fragmented, sectional illustration of the distal end of the extension wire of FIG. 9 inserted into the socket at the proximal end of the guidewire;

FIG. 11 is an illustration similar to FIG. 10 with the extension wire in a locked configuration.

DESCRIPTION OF THE ILLUSTRATIVE EMBODIMENT

Figure 1:
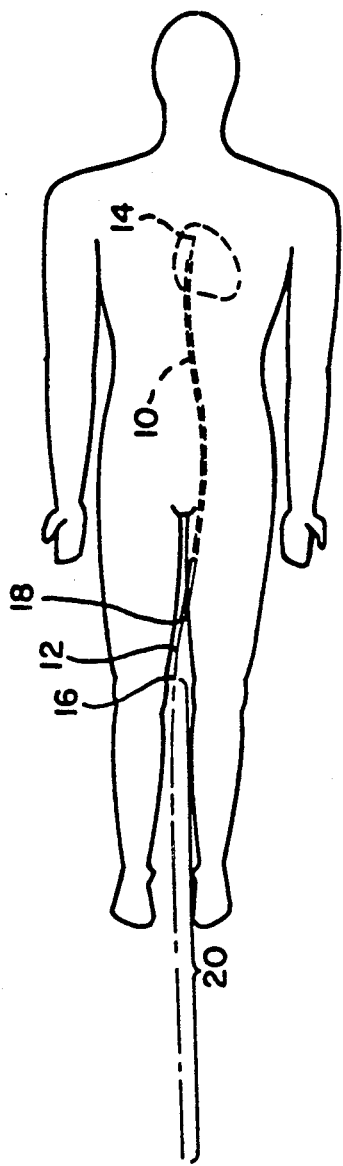
FIG. 1 is a diagrammatic illustration of a patient undergoing catheterization showing the guidewire and, in phantom, an exchange length wire.

FIG. 1 illustrates, in highly diagrammatic form, a catheter 10 and guidewire 12 which have been inserted into a patient s femoral artery and have been advanced through the region of the patient's heart where the desired procedure will be performed. The guidewire 12 and catheter 10 will have been inserted and placed in the artery in accordance with well known procedures. When it is desired to perform a catheter exchange, a conventional practice had been to remove the guidewire 12 from the catheter 10 and replace it with a long exchange wire. Then the catheter 10 could be removed over the exchange wire and the next catheter could be introduced into the patient over the exchange wire. Then the exchange wire would be removed and replaced with a shorter, conventional guidewire. As described in U.S. Pat. No. 4,917,103 and European Application No. 89304257.2 the foregoing procedure was improved with the development of the extendible guidewire system.

In accordance with the present invention, a further improved system is provided by which catheters may be exchanged without requiring removal of the guidewire 12 and without requiring the involvement attendant to the use of an exchange wire. In the practice of the present invention, the guidewire 12 is connected at its proximal end to an extension wire 20 while the guidewire 12 and catheter 10 remain in the patient. The extension wire 20 is attached securely to the proximal end of the guidewire 12 and serves to extend the effective length of the guidewire 12 sufficiently to permit the catheter 10 to be withdrawn over the guidewire 12 and extension 20. Each of the guidewire and extension wire may be coated with an appropriate lubricious material such as a suitable Teflon or silicone material as will be familiar with those in the art. Moreover, the present invention utilizes an improved connection between the guidewire and extension wire.

Figure 2:
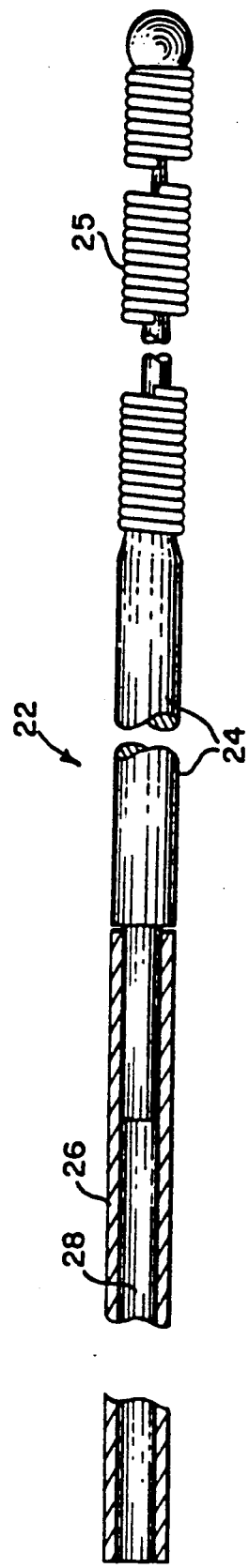
FIG. 2 is a fragmented, partly sectional illustration of a guidewire in accordance with the invention.

FIG. 2 shows a guidewire 22 modified in accordance with the present invention. The guidewire may be of the type illustrated in U.S. Pat. No. 4,545,390 to Leary having an elongate stainless steel shaft 24 having a proximal end (to the left in FIG. 2) and a distal end (to the right in FIG. 2) with a helical coil 25 mounted at its distal end. The guidewire, alternately, may be of a more conventional construction in which a helical coil extends substantially the full length of the guidewire. The Leary type of guidewire is disclosed by way of example.

Such a guidewire may, for example, be of the order of 175 cm long and may have a shaft 24 of a diameter of 0.018" or less. In the illustrative embodiment, the proximal end of the shaft 24 is fitted with a tubular member 26 having the same outer diameter of the shaft 24 and defining an elongate internal socket 28. The tubular member 26 may be formed from commercially available hypodermic tubing. Such tubing is seamed and has a somewhat roughened internal surface which may enhance the strength of the connection, as will be described. In the illustrative example, in which the outer diameter of the tubular member 26 is 0.012", the tubular member 26 may define a socket 28 that is about 5 to 8 cm deep and 0.008" in diameter. The edge of the tubular member 26 that defines the rim of the socket 28 preferably is rounded (see FIGS. 10, 11) so that the male element of the connector can be inserted smoothly and easily into the socket 28.

Figure 3:
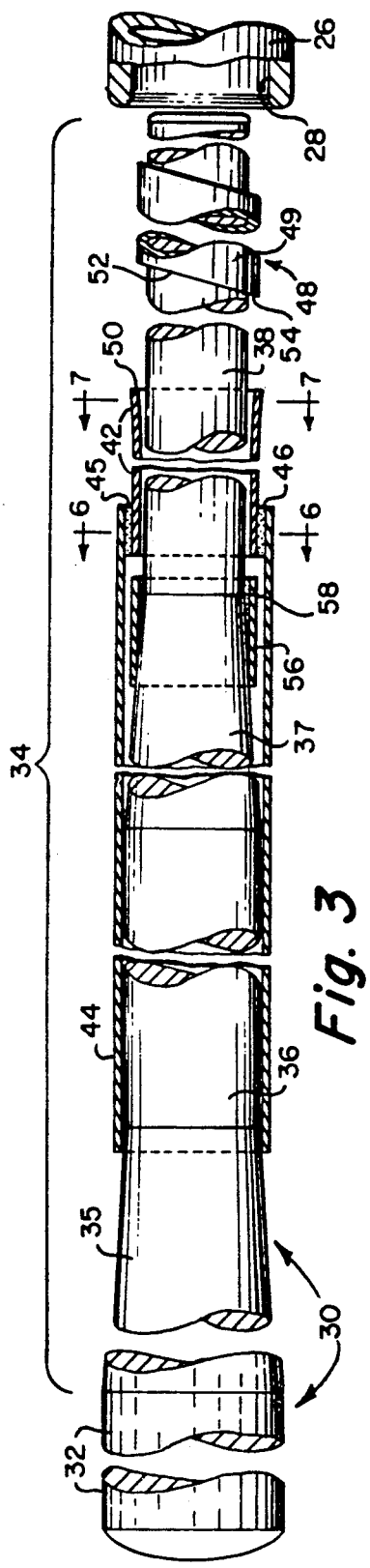
FIG. 3 is a fragmented, sectional illustration of one embodiment of the extension wire in accordance with the invention.

FIG. 3 is a fragmented illustration of the extension wire indicated generally by the reference character 30 with portions of the wire being axially compressed for clarity of illustration. The extension wire 30 may be considered as having a proximal end (to the left in FIG. 3) and a distal end (to the right in FIG. 3). The overall length of the extension wire 30 may be of the order of 145 cm which, when connected to a guidewire of 180 cm, results in a combined length of 325 cm which corresponds to the length of a conventional exchange wire used in femoral approach coronary angioplasty.

The extension wire 30 may be formed from a length of elongate, flexible stainless steel shaft 32. The distal end of the shaft 32 is formed to include a reduced diameter distally protecting core wire 34 that is smaller in diameter than the outer diameter of the body of the shaft. The reduced diameter core wire 34 may be formed by centerless grinding of the distal portion of the shaft using conventional centerless grinding techniques and equipment as will be familiar to those skilled in the art. In the embodiment shown in FIGS. 3-5, the core wire 34 is formed in a step tapered configuration which may include a proximal tapered segment 35 that reduces in diameter to a proximal barrel (uniform diameter) segment 36 which, in turn, leads to a distal tapered segment 37 which, in turn, leads to a distal barrel segment 38.

The connector arrangement at the distal end of the extension wire includes a thin walled sleeve 42 that is slidably disposed on the core wire 34. In the illustrative embodiment, the sleeve preferably is slidably disposed on the distal barrel segment 38.

In order to facilitate manipulation of the sleeve, the sleeve 42 may be provided with a larger diameter tubular handle 44 that is attached, at its distal end, to the proximal end of the sleeve 42, as by adhesive 45. The juncture of the distal end of the handle 44 and the proximal end of the sleeve 42 defines a shoulder 46 which serves as a stop element to limit the extent to which the sleeve 42 can be inserted into the tubular socket 28. The outer diameter of the tubular handle 44 is no greater than the diameter of the shaft 32 and tubular element 26 on the guidewire and is at least somewhat greater in diameter than the inner diameter of the tubular socket 28. As will be described, the physician may manipulate the axial position of the sleeve 42 by grasping and manipulating the handle 44.

The sleeve 42 may be formed from an appropriate polymeric material, such as a polyimide. Polyimide tubing is desirable for the sleeve because it is available in very thin walled tubes having very close tolerances. Additional desirable characteristics for use in the present invention are that the polyimide tubing displays good column strength, has a smooth surface and can be stretched somewhat radially while possessing memory such that after stretching, it will tend to return to its unstretched configuration. Such tubing is available from Polymicro Technologies of Phoenix, Arizona.

A wedging element, indicated generally by the reference character 48 serves as an expander element and is mounted to the distal end of the distal barrel 38 of the core wire 34. The wedging element 46 is constructed so that it may advance into the open distal end 50 of the sleeve 42 and is dimensioned in a manner to forcibly enlarge the effective diameter at the distal end 50 of the sleeve 42. The wedging element 48 thus is designed to interfere with distal advancement of the sleeve 42 relative to the core wire 34 and prevents the sleeve 42 from sliding off of the core 34. It will be appreciated, therefore, that by effecting relative movement of the wedging element 48 toward the sleeve 42, the wedging element 48 may become wedged in the outer open end 50 of the sleeve, with the outer open end of the sleeve 42 stretching and riding over and about the wedging element 48. The polymeric material from which the sleeve is made should be such as to permit some elastic radial expansion in the diameter of the sleeve, particularly in the distal end of the sleeve. The outer diameter of each of the relaxed sleeve and wedging element is substantially equal to or less than the inner diameter of the tubular socket so that the connector arrangement at the distal end of the extension wire can be inserted easily and with minimal resistance into the socket 28.

In the illustrative embodiment of the invention, the wedging element 48 may be formed from a tubular segment 49 securely attached to the distal end of the distal barrel segment 38. In this embodiment, the tubular segment 49 has an outer diameter just slightly greater than the inner diameter of sleeve 42, for example, of the order of 0.0005" greater. The tubular segment may be cut from a length of tubing, such as a polyimide tubing, and preferably is cut along a biased plane that lies at a non perpendicular angle to the longitudinal axis of the tube from which the element is cut. This may be seen in FIGS. 3-5 in which at least the proximally disposed edge 52 of the wedging element 48 lies at such a bias. The wedging element 48 may be securely attached to the distal end of the barrel segment 38 as by an appropriate adhesive, for example, cyanoacrylate. The purpose for forming the proximally facing edge of the wedging element at a bias is to permit the open distal end 50 of the sleeve 42 to engage the wedging element 48 in a gradual, progressive manner. Thus, it will be appreciated that the most proximally disposed portion 54 of the proximal edge 52 of the wedging element 48 will first engage a small portion of the distal end of the sleeve and then, as relative motion between the sleeve and core wire continues, the wedging element 48 will be drawn progressively into increased circumferential engagement with the distal opening 50 of the sleeve 42. In order to lessen the chance of the edge 52 becoming caught on the distal end of the sleeve 42, it may be desirable to form a smooth radius fillet at the juncture of the edge 52 and the segment 38 of the core wire 34. The fillet (not shown) could be formed from the same adhesive material (cyanoacrylate) used to attach the wedging element to the core. The foregoing arrangement provides a smooth and progressive advancement of the wedging element 48 into the open distal end 50 of the sleeve 42, thereby avoiding potential binding of the wedging element in the sleeve and providing for a progressively increasing wedging force on the end of the sleeve.

Figure 4:
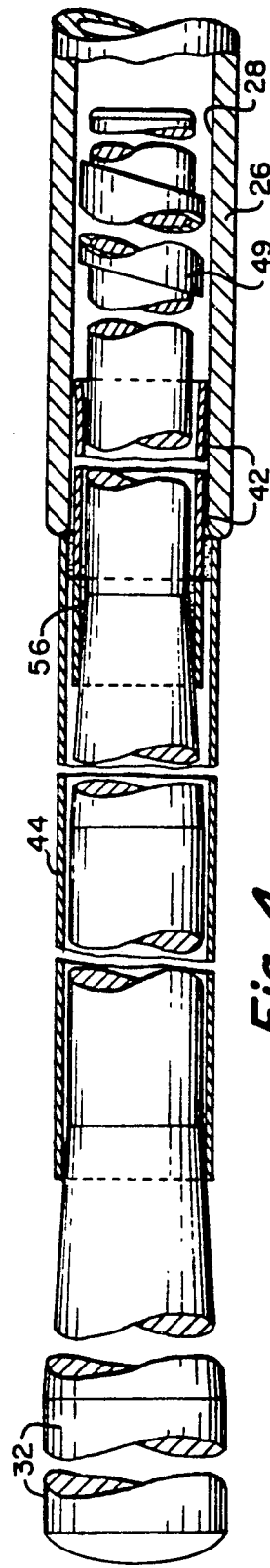
FIG. 4 is a fragmented, sectional illustration of the distal end of the extension wire of FIG. 3 inserted into the socket at the proximal end of the guidewire.

FIGS. 3 and 4 illustrate the distal end of the sleeve 42 as being somewhat flared. The tubing 42 initially is unflared but may become flared somewhat after the wedging element 48 has become wedged in the opening at the distal end 50 of the sleeve. After the wedging element 48 and sleeve 42 are separated, the distal end of the sleeve will have somewhat of a flare. The elastic memory of the material from which the sleeve is made, the flare will tend to contract and the distal end of the sleeve will closely approach its original unflared configuration. A very slight remaining flare, however, is advantageous in that it will facilitate entry of the wedging element 48 into the open end 50 of the sleeve. Should any flare be present at the distal end of the sleeve when it is desired to insert the sleeve into the socket 28, the smoothly rounded rim of the socket 28 will minimize the chance of the sleeve becoming caught on the rim of the socket.

It is desirable that the device be provided with a stop to limit the extent to which the sleeve can be drawn proximally. To that end, a tubular segment 56 having the same diameter and wall thickness as the sleeve 42 may be adhesively attached to the distal taper 37 by an adhesive bond 58. The stop may be formed simultaneously with assembly of the sleeve 42 onto the core wire 34. A convenient procedure includes selecting a tube for the sleeve that is slightly longer than required for the sleeve 42 by an amount equal to the intended length of the tubular stop 56. The extended length sleeve then can be placed over the distal end of the core wire 34 and brought into abutment with the distal taper 37. A circumferential slit then may be made at the proximal region of the sleeve 42 to sever the extended sleeve from the extended length that will correspond to the stop. The sleeve segment 42 then may be slid distally on the core wire 34 to expose the annular crevice between the cylindrical stop and the distal taper 37. A suitable adhesive 58, such as cyanoacrylate, may be permitted to wick (or may be injected into the annular space to securely attach the stop to the core wire.

Figure 5:
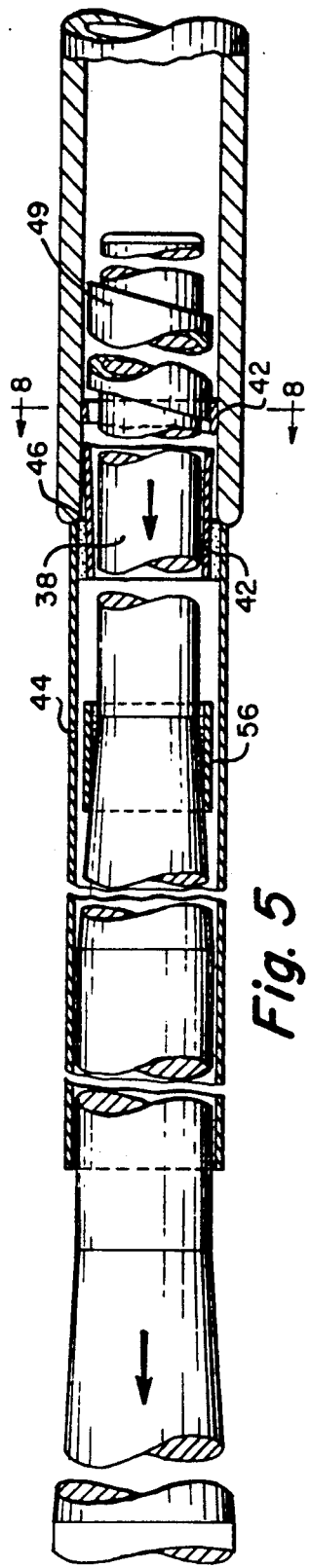
FIG. 5 is an illustration similar to FIG. 4 with the extension wire in a locked configuration.
Figure 7:
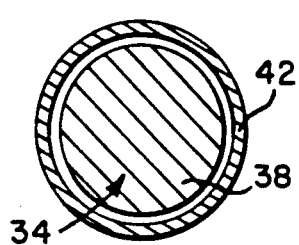
FIG. 7 is a sectional illustration of the device as seen along the line 7—7 of FIG. 3.
Figure 8:
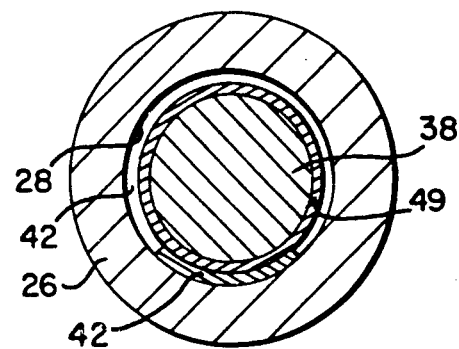
FIG. 8 is a sectional illustration through the connected and blocked connector elements as seen along the line 8—8 of FIG. 5.
Figure 6:
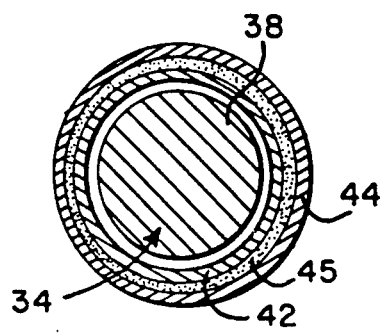
FIG. 6 is a sectional illustration through the device as seen along the line 6—6 of FIG. 3.

FIGS. 4 and 5 shows the manner in which the connection is made between the extension wire 30 and the guidewire. As shown in FIG. 3, the sleeve 42 is withdrawn proximally out of engagement with the wedging element 48. In that configuration, the core wire 34 and sleeve 48 are inserted into the socket 28 of the guidewire with the sleeve 42 being slid distally to cause the shoulder 46 to abut the proximal edge of the socket 28, as shown in FIG. 4. Then, by holding the handle 44 to maintain the position of the sleeve 42, the extension wire 20 is pulled in a proximal direction as suggested in FIG. 5 to cause the wedging element 48 to engage and become firmly wedged in the distal end 50 of the sleeve 42. The continued advancement of the wedging element into the end of the sleeve causes the distal end of the sleeve to expand radially into firm, secure engagement with the inner surface of the socket 28. The relatively rough surface of the socket 28 enhances the grip effected by the socket and outer sleeve.

In order to assure that the distal end 50 of the sleeve 42 will not snag on the rim of the socket 28, the rim of the socket is formed with a rounded contour, as may be seen in FIGS. 10 and 11. The rounded contour may be achieved by chemically etching the proximal end of the tubing 26.

The connection effected between the guidewire and the extension is very secure. Moreover, when the guidewire and extension wire do separate under a continually increasing load, it is not the connection that releases but, instead, it has been found that some part of the connection actually fractures.

The distal end of the extension wire may be inserted into the socket with very low resistance yet the force necessary to separate the connected elements is very substantial. It will be appreciated that once the guidewire and extension wire have been connected and the connection is locked, their connection will be very secure and they may be manipulated without concern of separation. Similarly, the extension will not become separated from the guidewire during catheter exchanges. Any tendency to pull the guidewire extension away from the guidewire will serve only to increase the wedging force applied to the sleeve thereby increasing the strength of the connection. When desired, the physician may separate easily the extension wire from the guidewire. All that is required is for the handle to be grasped and drawn proximally which pulls the distal end of the outer sleeve out from its wedged position between the inner sleeve and the inner surface of the socket 28.

An additional advantage of the invention is that when the guidewire and extension wire are mated, but remain unlocked, the guidewire may be rotated with respect to the extension wire. This may be desirable should the physician wish to manipulate and steer the guidewire while the guidewire remains mated with the extension wire.

By way of example, the guidewire may be of the order of 0.012" in diameter. The tubing 26 that defines the socket 28 on the proximal end of the guidewire may have an inner diameter about 0.007" to 0.008". The extension wire may have an elongate shaft 32 also of a diameter of 0.012". The step tapered core wire portion 40 extending over the segments 35, 36, 37 and 38 may be of the order of 5.0 cm in length. The proximal tapered segment 35 may be of the order of 0.6 cm long and may taper from 0.012" down to 0.009" at the diameter of the proximal barrel segment 36. The proximal barrel segment 36 may be 2.0 cm long. The distal taper 37 also may be 0.6 cm long and may taper down to 0.0045", the diameter of the distal barrel segment 38. The distal barrel segment 38 may be 2 cm long. The sleeve 42 may be of the order of 10.0 mm long, having an inner diameter of 0.006" and an outer diameter of 0.0075". The wedging element 48 may be formed from tubular polyimide stock having an inner diameter of 0.005" and an outer diameter of 0.0065". The tubular handle 44 may be of the order of 2.5 cm long having an inner diameter of 0.010"

Figure 12:
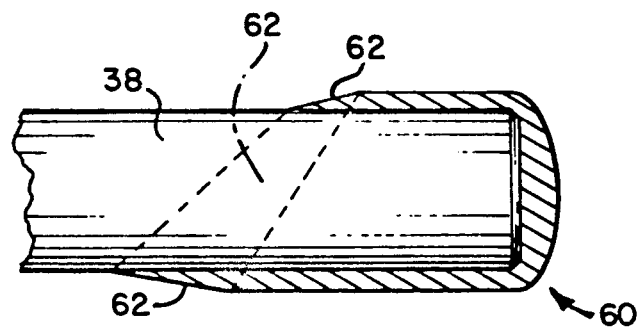
FIG. 12 is an illustration of the distal end of the extension wire of the embodiment of FIG. 9 illustrating an alternate manner of forming the wedging element.

FIGS. 9-11 illustrate another embodiment of the invention in which all of the elements are the same as that described above except that the wedging element 60 at the distal end of the core wire is in the form of a bulbous element having a proximally facing tapered surface 62. The bulbous wedging element 60 may be formed as a separate piece attached to the distal tip of the core wire (as suggested in FIG. 12) or, alternatively, may be formed by grinding the distal end of the wire 34 in a manner as to leave the bulbous wedging element 60. In this embodiment, the bulbous element may be cylindrical in cross section except for the proximally facing tapered portion 62. As shown, it is preferred that the taper be asymmetrical such that as the tapered wedging surface is drawn into the open distal end 50 of the sleeve 42, it will initially engage only a small portion of the circumference of the opening 50. As it continues its advancement into the open end of the sleeve, it will engage a progressively increasing circumferential portion of the open end thereby progressively increasing its wedging effect and thereby increasing the strength of the connection.

From the foregoing, it will be appreciated that the invention may be practiced using a sleeve 42 having a very thin wall. Accordingly, the outer diameter of the core 34 can be maximized. Consequently, the core 34 will be less fragile. Additionally, because the arrangement enables use of a relatively thick core wire, it is not necessary to reduce the diameter of the core wire to unacceptably small, fragile diameters in order to use the invention with smaller diameter guidewires. The present invention may be used with guidewire as small as 0.012" diameter and even smaller, of the order of 0.010".

It should be understood in the foregoing description the tubular socket was described as being formed on the proximal end of the guidewire with the sleeve mechanism on the distal end of the extension wire. It should be understood, however, that the parts may be reversed, that is, the invention may be practised with the socket on the distal end of the extension wire and the remaining connector elements on the proximal end of the guidewire.

Additionally, it will be appreciated that the invention may be used not only to connect a guidewire to a guidewire extension but also to connect a wire, such as a guidewire, to other tubular members, such as to a catheter, thereby to lock, temporarily the guidewire to the catheter.

From the foregoing, it will be appreciated that the invention provides an improved arrangement for detachably connecting a guidewire extension with a guidewire. The invention incorporates a manually operable mechanism for locking and unlocking the connection. The connective forces required are negligible yet the strength of the connection, when locked, is very substantial and assures that the extension and guidewire will not become inadvertently detached either during guidewire manipulation or during catheter exchanges. The arrangement can be used with a wide range of guidewire sizes and, particularly, with very small diameter guidewire.

It should be understood, however, that the foregoing description of the invention is intended merely to be illustrative thereof and that other modifications, embodiments and equivalents may be apparent to those skilled in the art without departing from the spirit.

Having thus described the invention, what I desire to claim and secure by Letters Patent is:

1. An extendible guidewire system for guiding an elongate, flexible catheter having a guidewire lumen through a lumen in the body of a patient and adapted to facilitate exchange of the catheter for another catheter comprising:
   a guidewire having a proximal end and a distal end;
   an extension wire having a proximal end and a distal end;
   the proximal end of the guidewire and the distal end of the extension wire being connectibly matable with each other, the connection between said mating ends including a manually operable mechanism movable between positions for locking and unlocking the connection the locking mechanism being movable independently of mating of said ends.

2. An extendible guidewire system as defined in claim 1 wherein the movable portions of the mechanism are carried by one of the wires.

3. An extendible guidewire system for guiding an elongate, flexible catheter having a guidewire lumen through a lumen in the body of the patient and adapted to facilitate exchange of the catheter for another catheter comprising:

a guidewire having a proximal end and a distal end;
an extension wire having a proximal end and a distal end;
the proximal end of the guidewire and the distal end of the extension wire being connectibly matable with each other, the connection between said mating ends including a manually-operable mechanism movable between positions for locking and unlocking the connection;
said locking mechanism further comprising:
one of the wires having a socket formed at its mating end;
the other wire having, at its mating end, a radially expandable element;
an expander element carried by the other wire for radially expanding the expandable element when the expandable element is disposed within the socket;
the radially expandable element and expander element being insertable into the socket in a disengaged configuration.

4. An extendible guidewire system as defined in claim 3 wherein the expandable element comprises a sleeve slidable on the end of said other wire and wherein the expander element is mounted on the end of said other wire whereby relative movement between the sleeve and the other wire may cause engagement of the expander element with the sleeve to effect radial expansion of at least a portion of the sleeve.

5. An extendible guidewire system as defined in claim 4 wherein the expander element is constructed and arranged to be wedged into the open end of the sleeve.

6. An extendible guidewire system as defined in claim 5 wherein the expander is in the form of an enlarged element at the end of the wire and has a surface facing an open end of the sleeve, the facing surface being tapered toward the sleeve.

7. An extendible guidewire system as defined in claim 6 wherein the wedge is formed with an asymmetrical taper whereby it may engage the periphery of the open end in the sleeve progressively.

8. An extendible guidewire system as defined in claim 5 wherein the expander element is in the form of a segment of a tube mounted to the end of a wire and having an edge facing the end of the sleeve, said facing edge extending in an oblique direction that is not perpendicular to the axis of the tube.

9. An extendible guidewire system as defined in claim 4 further comprising:

stop means for limiting the extent to which the sleeve can be inserted into the socket.

10. An extendible guidewire system as defined in any one of claims 4–8 further comprising:

a handle attached to the proximal end of the sleeve and extending proximally therefrom.

11. An extendible guidewire system as defined in claim 9 further comprising:

a tubular handle attached to the outside of the proximal end of the sleeve thereby defining a shoulder at the juncture with the sleeve, the shoulder being dimensioned to be alignable with the end of the tubular wall that defines the socket.

12. An extendible guidewire system as defined in claim 4 further comprising:

a stop carried on the wire to limit the proximal position of the sleeve.

13. An extendible guidewire system as defined in any of claims 1–5 wherein the guidewire and extension wire diameter lie between about 0.013" to about 0.014" in diameter.

14. An extendible guidewire system as defined in any of claims 1–5 wherein the guidewire and extension wire diameter lie between about 0.012" to about 0.013" in diameter.

15. An extendible guidewire system as defined in any of claims 1–5 wherein the guidewire and extension wire diameter lie between about 0.011" to about 0.012" in diameter.

16. An extendible guidewire system as defined in any of claims 1–5 wherein the guidewire and extension wire diameter lie between about 0.010" to about 0.011" in diameter.

17. An extendible guidewire system as defined in any of claims 3–5 wherein the socket is on the guidewire and the movable mechanism is on the extension wire.

18. An extendible guidewire system as defined in any of claims 3–5 wherein the socket is on the extension wire and the movable mechanism is on the guidewire.

19. An extendable guidewire extension system as defined in any one of claims 3–8 wherein the expandable element is formed from an elastically yieldable polymeric material.

20. A connector system for connecting a medical guidewire to a tubular member comprising:

an elongate sleeve slidably mounted on the guidewire;
an expander element carrier by the guidewire and being engageable an end of the sleeve, the expander element and sleeve being constructed and arranged so that when the expander element engages an end of the sleeve, it will cause the sleeve to expand radially;
the guidewire, expander element and sleeve being insertable into the tubular member when the expander element and sleeve are disengaged.

21. A connector system as defined in claim 20 wherein the tubular member is disposed on another wire.

22. A connector system as defined in claim 20 wherein the tubular member comprises a portion of the catheter.

* * * * *